(12) United States Patent
Bailon

(10) Patent No.: US 6,583,272 B1
(45) Date of Patent: Jun. 24, 2003

(54) ERYTHROPOIETIN CONJUGATES

(75) Inventor: Pascal Sebastian Bailon, Florham Park, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 60 days.

(21) Appl. No.: 09/604,938

(22) Filed: Jun. 27, 2000

Related U.S. Application Data

(60) Provisional application No. 60/142,254, filed on Jul. 2, 1999, provisional application No. 60/150,225, filed on Aug. 23, 1999, provisional application No. 60/151,548, filed on Aug. 31, 1999, and provisional application No. 60/166,151, filed on Nov. 17, 1999.

(51) Int. Cl.$^7$ .................... C07K 14/505; C07K 17/00; A61K 38/17; A61K 39/00
(52) U.S. Cl. .................... 530/397; 530/350; 514/2; 514/8; 424/194.1; 424/195.11
(58) Field of Search .................... 514/2, 8; 530/350, 530/397; 424/195.11, 194.1

(56) References Cited

U.S. PATENT DOCUMENTS

| | | | |
|---|---|---|---|
| 4,179,337 A | | 12/1979 | Davis et al. ............... 435/181 |
| 4,806,524 A | | 2/1989 | Kawaguchi et al. .......... 514/8 |
| 4,902,502 A | | 2/1990 | Nitecki et al. |
| 4,917,888 A | | 4/1990 | Katre et al. |
| 5,641,663 A | * | 6/1997 | Garvin et al. ............ 435/172.1 |
| 5,672,662 A | | 9/1997 | Harris et al. |
| 5,681,811 A | | 10/1997 | Ekwuribe ................ 518/8 |
| 6,340,742 B1 | * | 1/2002 | Burg et al. ............... 530/351 |

FOREIGN PATENT DOCUMENTS

| | | |
|---|---|---|
| EP | 0154316 | 2/1985 |
| EP | 0605963 | 7/1993 |
| EP | 640619 | 3/1995 |
| EP | 668 353 | 8/1995 |
| EP | 0741187 | 11/1996 |
| WO | WO 95/05465 | * 2/1995 |
| WO | WO 9911781 | 3/1999 |
| WO | WO 00 32772 | 6/2000 |
| WO | WO 01 02017 | 1/2001 |
| WO | WO 01 68141 | 9/2001 |
| WO | WO 01 76640 | 10/2001 |
| WO | WO 01 87329 | 11/2001 |

OTHER PUBLICATIONS

Pascal Bailon and Wolfgang Berthold, Polyethylene glycol–conjugated pharmaceutical proteins (PSTT) vol. 1, No. 8, Nov. 1998, pp. 352–356.

* cited by examiner

Primary Examiner—Gary Kunz
Assistant Examiner—Regina M. DeBerry
(74) Attorney, Agent, or Firm—George W. Johnston; Patricia S. Rocha-Tramaloni

(57) ABSTRACT

Conjugates of erythropoietin with poly(ethylene glycol) comprise an erythropoietin glycoprotein having at least one free amino group and having the in vivo biological activity of causing bone marrow cells to increase production of reticulocytes and red blood cells and selected from the group consisting of human erythropoietin and analogs thereof which have sequence of human erythropoietin modified by the addition of from 1 to 6 glycosylation sites or a rearrangement of at least one glycosylation site; the glycoprotein being covalently linked to "n" poly(ethylene glycol) groups of the formula $-CO-(CH_2)_x(OCH_2CH_2)_m-OR$ with the carbonyl of each poly(ethylene glycol) group forming an amide bond with one of said amino groups; wherein R is lower alkyl; x is 2 or 3; m is about 450 to about 900; n is from 1 to 3; and n and m are chosen so that the molecular weight of the conjugate minus the erythropoietin glycoprotein is from 20 kilodaltons to 100 kilodaltons.

15 Claims, 3 Drawing Sheets

SEQUENCE LISTING

<160> NUMBER OF SEQ ID NOS: 3

<210> SEQ ID NO 1
<211> LENGTH: 165
<212> TYPE: PRT
<213> ORGANISM: Homo sapiens

```
<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 28
```

```
<212> TYPE: PRT
<213> ORGANISM: Homo sapiens

<400> SEQUENCE: 3

Ser Ser Ser Ser Lys Ala Pro Pro Pro Ser Leu Pro Ser Pro Ser Arg
  1               5                  10                  15

Leu Pro Gly Pro Ser Asp Thr Pro Ile Leu Pro Gln
            20                  25
```

ERYTHROPOIETIN CONJUGATES

CROSS-REFERENCE TO RELATED APPLICATIONS

The priority of U.S. Provisional Application No. 60/142,254, filed Jul. 2, 1999; No. 60/150,225, filed Aug. 23, 1999; No. 60/151,548, filed Aug. 31, 1999; and No. 60/166,151, filed Nov. 17, 1999 is claimed.

BACKGROUND OF THE INVENTION

Erythropoiesis is the production of red blood cells, which occurs to offset cell destruction. Erythropoiesis is a controlled physiological mechanism that enables sufficient red blood cells to be available for proper tissue oxygenation. Naturally occurring human erythropoietin (hEPO) is produced in the kidney and is the humoral plasma factor which stimulates red blood cell production (Carnot, P and Deflandre, C (1906) C. R. Acad. Sci. 143: 432; Erslev, A J (1953 Blood 8: 349; Reissmann, K R (1950) Blood 5: 372; Jacobson, L O, Goldwasser, E, Freid, W and Plzak, L F (1957) Nature 179: 6331–4). Naturally occurring EPO stimulates the division and differentiation of committed erythroid progenitors in the bone marrow and exerts its biological activity by binding to receptors on erythroid precursors (Krantz, B S (1991) Blood 77: 419).

Erythropoietin has been manufactured biosynthetically using recombinant DNA technology (Egrie, J C, Strickland, T W, Lane, J et al. (1986) Immunobiol. 72: 213–224) and is the product of a cloned human EPO gene inserted into and expressed in the ovarian tissue cells of the chinese hamster (CHO cells). The primary structure of the predominant, fully processed form of hEPO is illustrated in SEQ ID NO:1. There are two disulfide bridges between $Cys^7$-$Cys^{161}$ and $Cys^{29}$-$Cys^{33}$. The molecular weight of the polypeptide chain of EPO without the sugar moieties is 18,236 Da. In the intact EPO molecule, approximately 40% of the molecular weight are accounted for by the carbohydrate groups that glycosylate the protein at glycosylation sites on the protein (Sasaki, H, Bothner, B, Dell, A and Fukuda, M (1987) J. Biol. Chem. 262: 12059).

Because human erythropoietin is essential in red blood cell formation, the hormone is useful in the treatment of blood disorders characterized by low or defective red blood cell production. Clinically, EPO is used in the treatment of anemia in chronic renal failure patients (CRF) (Eschbach, J W, Egri, J C, Downing, M R et al. (1987) NEJM 316: 73–78; Eschbach, J W, Abdulhadi, M H, Browne, J K et al. (1989) Ann. Intern. Med. 111: 992; Egrie, J C, Eschbach, J W, McGuire, T, Adamson, J W (1988) Kidney Intl. 33: 262; Lim, V S, Degowin, R L, Zavala, D et al. (1989) Ann. Intern. Med. 110: 108–114) and in AIDS and cancer patients undergoing chemotherapy (Danna, R P, Rudnick, S A, Abels, R I In: M B, Garnick, ed. Erythropoietin in Clinical Applications—An International Perspective. New York, N.Y.: Marcel Dekker; 1990: p. 301–324). However, the bioavailability of commercially available protein therapeutics such as EPO is limited by their short plasma half-life and susceptibility to protease degradation. These shortcomings prevent them from attaining maximum clinical potency.

SUMMARY OF THE INVENTION

This invention provides an erythropoietin conjugate, said conjugate comprising an erythropoietin glycoprotein having at least one free amino group and having the in vivo biological activity of causing bone marrow cells to increase production of reticulocytes and red blood cells and selected from the group consisting of human erythropoietin and analogs thereof which have sequence of human erythropoietin modified by the addition of from 1 to 6 glycosylation sites or a rearrangement of at least one glycosylation site; said glycoprotein being covalently linked to "n" poly(ethylene glycol) groups of the formula —CO—$(CH_2)_x$—$OCH_2CH_2)_m$—OR with the —CO (i.e. carbonyl) of each poly(ethylene glycol) group forming an amide bond with one of said amino groups; wherein R is lower alkyl; x is 2 or 3; m is from about 450 to about 900; n is from 1 to 3; and n and m are chosen so that the molecular weight of the conjugate minus the erythropoietin glycoprotein is from 20 kilodaltons to 100 kilodaltons. This invention further provides compositions containing conjugates described herein in which the percentage of conjugates in the composition in which n is 1 is at least ninety percent.

Compared to unmodified EPO (i.e., EPO without a PEG attached) and conventional PEG-EPO conjugates, the present conjugates have an increased circulating half-life and plasma residence time, decreased clearance, and increased clinical activity in vivo. The conjugates of this invention have the same uses as EPO. In particular, the conjugates of this invention are useful to treat patients by stimulating the division and differentiation of committed erythroid progenitors in the bone marrow in the same way EPO is used to treat patients.

DETAILED DESCRIPTION OF THE INVENTION

Figure 1:
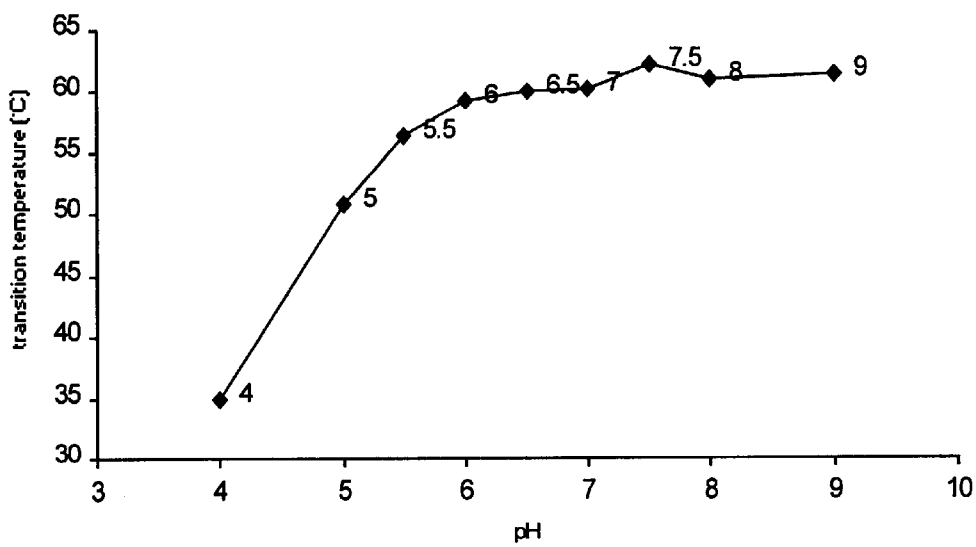
FIG. 1: Influence of pH on thermal stability. The transition temperature is plotted against the pH.

This invention provides conjugates, said conjugates comprising an erythropoietin glycoprotein having at least one free amino group and having the in vivo biological activity of causing bone marrow cells to increase production of reticulocytes and red blood cells and selected from the group consisting of human erythropoietin and analogs thereof which have sequence of human erythropoietin modified by the addition of from 1 to 6 glycosylation sites or a rearrangement of at least one glycosylation site; said glycoprotein being covalently linked to "n" poly(ethylene glycol) groups of the formula —CO—$(CH_2)_x$—$(OCH_2CH_2)_m$—OR with the —CO (i.e. carbonyl) of each poly(ethylene glycol)

group forming an amide bond with one of said amino groups; wherein R is lower alkyl; x is 2 or 3; m is from about 450 to about 900; n is from 1 to 3; and n and m are chosen so that the molecular weight of the conjugate minus the erythropoietin glycoprotein is from 20 kilodaltons to 100 kilodaltons.

It has been found that the conjugates of this invention can be used in the same manner as unmodified EPO. However, the conjugates of this invention have an increased circulating half-life and plasma residence time, decreased clearance, and increased clinical activity in vivo. Because of these improved properties, the conjugates of this invention can be administered once weekly instead of the three times weekly for unmodified EPO. Decreased frequency of administration is expected to result in improved patient compliance leading to improved treatment outcomes, as well as improved patient quality of life. Compared to conventional conjugates of EPO linked to poly(ethylene glycol) it has been found that conjugates having the molecular weight and linker structure of the conjugates of this invention have an improved potency, stability, AUC, circulating half-life, and cost of goods profile.

The conjugates in accordance of this invention can be administered in a therapeutically effective amount to patients in the same way EPO is administered. The therapeutically effective amount is that amount of conjugate necessary for the in vivo biological activity of causing bone marrow cells to increase production of reticulocytes and red blood cells. The exact amount of conjugate is a matter of preference subject to such factors as the exact type of condition being treated, the condition of the patient being treated, as well as the other ingredients in the composition. The pharmaceutical compositions containing the conjugate may be formulated at a strength effective for administration by various means to a human patient experiencing blood disorders characterized by low or defective red blood cell production. Average therapeutically effective amounts of the conjugate may vary and in particular should be based upon the recommendations and prescription of a qualified physician.

The erythropoietin glycoprotein products prepared in accordance with this invention may be prepared in pharmaceutical compositions suitable for injection with a pharmaceutically acceptable carrier or vehicle by methods known in the art. Among the preferred pharmaceutically acceptable carriers for formulating the products of the invention are human serum albumn, human plasma proteins, etc.

The term "erythropoietin" or "EPO" refers to a glycoprotein, having the amino acid sequence set out in (SEQ ID NO: 1) or (SEQ ID NO: 2) or an amino acid sequence substantially homologous thereto, whose biological properties relate to the stimulation of red blood cell production and the stimulation of the division and differentiation of committed erythroid progenitors in the bone marrow. As used herein, these terms include such proteins modified deliberately, as for example, by site directed mutagenesis or accidentally through mutations. These terms also include analogs having from 1 to 6 additional sites for glycosylation, analogs having at least one additional amino acid at the carboxy terminal end of the glycoprotein, wherein the additional amino acid includes at least one glycosylation site, and analogs having an amino acid sequence which includes a rearrangement of at least one site for glycosylation. These terms include both natural and recombinantly produced human erythropoietin. The erythropoietin conjugates of this invention can be represented by Formula 1:

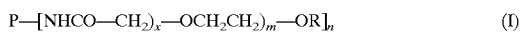

(I)

wherein x, m, n and R are as above. In Formula I, P is the residue of an erythropoietin glycoprotein described herein, (i.e. without the amino group or amino groups which form an amide linkage with the carbonyl shown in Formula I), having the in vivo biological activity of causing bone marrow cells to increase production of reticulocytes and red blood cells. P may be selected from the group consisting of residues of human erythropoietin and analogs thereof having from 1 to 6 additional sites for glycosylation. As set out in detail below, the preparation and purification of EPO are well known in the art. By EPO is meant the natural or recombinant protein, preferably human, as obtained from any conventional source such as tissues, protein synthesis, cell culture with natural or recombinant cells. Any protein having the. activity of EPO, such as muteins or otherwise modified proteins, is encompassed. Recombinant EPO may be prepared via expression in CHO—, BHK— or HeLa cell lines, by recombinant DNA technology or by endogenous gene activation. Expression of proteins, including EPO, by endogenous gene activation is well known in the art and is disclosed, for example in U.S. Pat. Nos. 5,733,761, 5,641, 670, and 5,733,746, and international patent publication Nos. WO 93/09222, WO 94/12650, WO 95/31560, WO 90/11354, WO 91/06667 and WO 91/09955, the contents of each of which are incorporated herein by reference. The preferred EPO species for the preparation of erythropoietin glycoprotein products are human EPO species. More preferably, the EPO species is the human EPO having the amino acid sequence set out in SEQ ID NO:1 or SEQ ID NO:2, more preferably the amino acid sequence SEQ ID NO:1.

In an embodiment, P may be the residue of a glycoprotein analog having from 1 to 6 additional sites for glycosylation. Glycosylation of a protein, with one or more oligosaccharide groups, occurs at specific locations along a polypeptide backbone and greatly affects the physical properties of the protein such as protein stability, secretion, subcellular localization, and biological activity. Glycosylation is usually of two types. O-linked oligosaccharides are attached to serine or threonine residues and N-linked oligosaccharides are attached to asparagine residues. One type of oligosaccharide found on both N-linked and O-linked oligosaccharides is N-acetylneuraminic acid (sialic acid), which is a family of amino sugars containing 9 or more carbon atoms. Sialic acid is usually the terminal residue on both N-linked and O-linked oligosaccharides and, because it bears a negative charge, confers acidic properties to the glycoprotein. Human erythropoietin, having 165 amino acids, contains three N-linked and one O-linked oligosaccharide chains which comprise about 40% of the total molecular weight of the glycoprotein. N-linked glycosylation occurs at asparagine residues located at positions 24, 38, and 83 and O-linked glycosylation occurs at a serine residue located at position 126. The oligosaccharide chains are modified with terminal sialic acid residues. Enzymatic removal of all sialic acid residues from the glycosylated erythropoietin results in loss of in vivo activity but not in vitro activity because sialylation of erythropoietin prevents its binding, and subsequent clearance, by hepatic binding protein.

The glycoproteins of the present invention include analogs of human erythropoietin with one or more changes in the amino acid sequence of human erythropoietin which result in an increase in the number of sites for sialic acid attachment. These glycoprotein analogs may be generated by site-directed mutagenesis having additions, deletions, or substitutions of amino acid residues that increase or alter sites that are available for glycosylation. Glycoprotein analogs having levels of sialic acid greater than those found in human erythropoietin are generated by adding glycosylation sites which do not perturb the secondary or tertiary conformation required for biological activity. The glycoproteins of the present invention also include analogs having increased levels of carbohydrate attachment at a glycosylation site which usually involve the substitution of one or more amino acids in close proximity to an N-linked or O-linked site. The glycoproteins of the present invention also include analogs having one or more amino acids extending from the carboxy terminal end of erythropoietin and providing at least one additional carbohydrate site. The glycoproteins of the present invention also include analogs having an amino acid sequence which includes a rearrangement of at least one site for glycosylation. Such a rearrangement of glycosylation site involves the deletion of one or more glycosylation sites in human erythropoietin and the addition of one or more non-naturally occurring glycosylation sites. Increasing the number of carbohydrate chains on erythropoietin, and therefore the number of sialic acids per erythropoietin molecules may confer advantageous properties such as increased solubility, greater resistance to proteolysis, reduced immunogenecity, increased serum half-life, and increased biological activity. Erythropoietin analogs with additional glycosylation sites are disclosed in more detail in European Patent Application 640 619, to Elliot published March 1, 1995.

In a preferred embodiment, the glycoproteins of the present invention comprise an amino acid sequence which includes at least one additional site for glycosylation such as, but not limited to, erythropoietins comprising the sequence of human erythropoietin modified by a modification selected from the following:
$Asn^{30}Thr^{32}$;
$Asn^{51}Thr^{53}$;
$Asn^{57}Thr^{59}$;
$Asn^{69}$;
$Asn^{69}Thr^{71}$;
$Ser^{68}Asn^{69}Thr^{71}$;
$Val^{87}Ans^{88}Thr^{90}$;
$Ser^{87}Asn^{88}Thr^{90}$;
$Ser^{87}Asn^{88}Gly^{89}Thr^{90}$;
$Ser^{87}Asn^{88}Thr^{90}Thr^{92}$;
$Ser^{87}Asn^{88}Thr^{90}Ala^{162}$;
$Asn^{69}Thr^{71}Ser^{87}Asn^{88}Thr^{90}$;
$Asn^{30}Thr^{32}Val^{87}Asn^{88}Thr^{90}$;
$Asn^{89}Ile^{90}Thr^{91}$;
$Ser^{87}Asn^{89}Ile^{90}Thr^{91}$;
$Asn^{136}Thr^{138}$;
$Asn^{138}Thr^{140}$;
$Thr^{125}$; and
$Pro^{124}Thr^{125}$.

The notation used herein for modification of amino acid sequence means that the position(s) of the corresponding unmodified protein (e.g. hEPO of SEQ ID NO:1 or SEQ ID NO:2) indicated by the superscripted number(s) is changed to the amino acid(s) that immediately precede the respective superscripted number(s).

The glycoprotein may also be an analog having at least one additional amino acid at the carboxy terminal end of the glycoprotein, wherein the additional amino acid includes at least one glycosylation site. The additional amino acid may comprise a peptide fragment derived from the carboxy terminal end of human chorionic gonadotropin. Preferably, the glycoprotein is an analog selected from the group consisting of (a) human erythropoietin having the amino acid sequence, Ser Ser Ser Ser Lys Ala Pro Pro Pro Ser Leu Pro Ser Pro Ser Arg Leu Pro Gly Pro Ser Asp Thr Pro Ile Leu Pro Gln (SEQ ID NO:3), extending from the carboxy terminus; (b) the analog in (a) further comprising $Ser^{87}$ $Asn^{88}$ $Thr^{90}$ EPO; and (c) the analog in (a) further comprising $Asn^{30}Thr^{32}$ $Val^{87}$ $Asn^{88}$ $Thr^{90}$ EPO.

The glycoprotein may also be an analog having an amino acid sequence which includes a rearrangement of at least one site for glycosylation. The rearrangement may comprise a deletion of any of the N-linked carbohydrate sites in human erythropoietin and an addition of an N-linked carbohydrate site at position 88 of the amino acid sequence of human erythropoietin. Preferably, the glycoprotein is an analog selected from the group consisting of $Gln^{24}$ $Ser^{87}$ $Asn^{88}$ $Thr^{90}$ EPO; $Gln^{38}$ $Ser^{87}$ $Asn^{88}$ $Thr^{90}$ EPO; and $Gln^{83}$ $Ser^{87}$ $Asn^{88}$ $Thr^{90}$ EPO.

As used herein, "lower alkyl" means a linear or branched alkyl group having from one to six carbon atoms. Examples of lower alkyl groups include methyl, ethyl and isopropyl. In accordance with this invention, R is any lower alkyl. Conjugates in which R is methyl are preferred.

The symbol "m" represents the number of ethylene oxide residues ($OCH_2CH_2$) in the poly(ethylene oxide) group. A single PEG subunit of ethylene oxide has a molecular weight of about 44 daltons. Thus, the molecular weight of the conjugate (excluding the molecular weight of the EPO) depends on the number "m". In the conjugates of this invention "m" is from about 450 to about 900 (corresponding to a molecular weight of about 20 kDa to about 40 kDa), preferably from about 650 to about 750 (corresponding to a molecular weight of about 30 kDa). The number m is selected such that the resulting conjugate of this invention has a physiological activity comparable to unmodified EPO, which activity may represent the same as, more than, or a fraction of the corresponding activity of unmodified EPO. A molecular weight of "about" a certain number means that it is within a reasonable range of that number as determined by conventional analytical techniques. The number "m" is selected so that the molecular weight of each poly(ethylene glycol) group covalently linked to the erythropoietin glycoprotein is from about 20 kDa to about 4 kDa, and is preferably about 30 kDa.

In the conjugates of this invention, the number "n is the number of polyethylene glycol groups covalently bound to free amino groups (including ε-amino groups of a lysine amino acid and/or the amino-terminal amino group) of an erythropoietin protein via amide linkage(s). A conjugate of this invention may have one, two, or three PEG groups per molecule of EPO. "n" is an integer ranging from 1 to 3, preferably "n" is 1 or 2, and more preferably "n" is 1.

The compound of Formula I can be prepared from the known polymeric material:

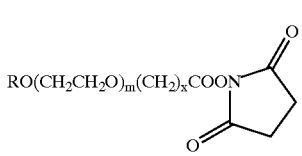

(II)

in which R and m are as described above, by condensing the compound of Formula II with the erythropoietin glycoprotein. Compounds of Formula II in which x is 3 are alpha-lower alkoxy, butyric acid succinimidyl esters of poly(ethylene glycol) (lower alkoxy-PEG-SBA). Compounds of Formula II in which x is 2 are alpha-lower alkoxy, propionic acid succinimidyl esters of poly(ethylene glycol) (lower alkoxy-PEG-SPA). Any conventional method of reacting an activated ester with an amine to form an amide can be utilized. In the reaction described above, the exemplified succinimidyl ester is a leaving group causing the amide formation. The use of succinimidyl esters such as the compounds of formula II to produce conjugates with proteins are disclosed in U.S. Pat. No. 5,672,662, issued Sept. 30, 1997 (Harris, et al.).

Human EPO contains nine free amino groups, the amino-terminal amino group plus the ε-amino groups of 8 lysine residues. When the pegylation reagent was combined with a SBA compound of Formula II, it has been found that at pH 7.5, a protein:PEG ratio of 1:3, and a reaction temperature of from 20–25° C., a mixture of mono-, di-, and trace amounts of the tri-pegylated species were produced. When the pegylation reagent was a SPA compound of Formula II, at similar conditions except that the protein:PEG ratio was 1:2, primarily the mono-pegylated species is produced. The pegylated EPO can be administered as a mixture, or as the cation exchange chromatography separated different pegylated species. By manipulating the reaction conditions (e.g., ratio of reagents, pH, temperature, protein concentration, time of reaction etc.), the relative amounts of the different pegylated species can be varied.

Human erythropoietin (EPO) is a human glycoprotein which stimulates the formation of erythrocytes. Its preparation and therapeutic application are described in detail for example in U.S. Pat. Nos. 5,547,933 and 5,621,080, EP-B 0 148 605, Huang, S. L., Proc. Natl. Acad. Sci. USA (1984) 2708–2712, EP-B 0 205 564, EP-B 0 209 539 and EP-B 0 411 678 as well as Lai, P. H. et al., J. Biol. Chem. 261 (1986) 3116–3121, an Sasaki, H. et al., J. Biol. Chem. 262 (1987) 12059–12076. Erythropoietin for therapeutic uses may be produced by recombinant means (EP-B 0 148 605, EP-B 0 209 539 and Egrie, J. C., Strickland, T. W., Lane, J. et al. (1986) Immunobiol. 72: 213–224).

Methods for the expression and preparation of erythropoietin in serum free medium are described for example in WO 96/35718, to Burg published Nov. 14, 1996, and in European Patent Publication No. 513 738, to Koch published Jun. 12, 1992. In addition to the publications mentioned above, it is known that a serum-free fermentation of recombinant CHO cells which contain an EPO gene can be carried out. Such methods are described for example in EP-A 0 513 738, EP-A 0 267 678 and in a general form by Kawamoto, T. et al., Analytical Biochem. 130 (1983) 445–453, EP-A 0 248 656, Kowar, J. and Franek, F., Methods in Enzymology 421 (1986) 277–292, Bavister, B., Expcology 271 (1981) 45–51, EP-A 0 481 791, EP-A 0 307 247, EP-A 0 343 635, WO 88/00967.

In EP-A 0 267 678 an ion exchange chromatography on S-Sepharose, a preparative reverse phase HPLC on a $C_8$ column and a gel filtration chromatography are described for the purification of EPO produced in serum-free culture after dialysis. In this connection the gel filtration chromatography step can be replaced by ion exchange chromatography on S-Sepharose fast flow. It is also proposed that a dye chromatography on a Blue Trisacryl column be carried out before the ion exchange chromatography.

A process for the purification of recombinant EPO is described by Nobuo, I. et al., J. Biochem. 107 (1990) 352–359. In this process EPO is treated however with a solution of Tween® 20, phenylmethylsulfonyl fluoride, ethylmaleimide, pepstatin A, copper sulfate and oxamic acid prior to the purification steps. Publications, including WO 96/35718, to Burg published Nov. 14, 1996, discloses a process for preparing erythropoietin in a serum free fermentation process (EPOsf).

The specific activity of EPO or EPO conjugates in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects. The biological activity of the EPO proteins, or fragments thereof, obtained and purified in accordance with this invention can be tested by methods according to Annable, et al., Bull. Wld. Hlth. Org. (1972) 47: 99–112 and Pharm. Europa Spec. Issue Erythropoietin BRP Bio 1997(2). Another biological assay for determining the activity of EPO protein, the normocythaemic mouse assay, is described in Example 4. This invention provides a composition comprised of conjugates as described above. A composition containing at least ninety percent mono-PEG conjugates, i.e. in which n is 1, can be prepared as shown in Example 5. Usually mono-PEG conjugates of erythropoietin glycoproteins are desirable because they tend to have higher activity than di-PEG conjugates. The percentage of mono-PEG conjugates as well as the ratio of mono- and di-PEG species can be controlled by pooling broader fractions around the elution peak to decrease the percentage of mono-PEG or narrower fractions to increase the percentage of mono-PEG in the composition. About ninety percent mono-PEG conjugates is a good balance of yield and activity. Sometimes compositions in which, for example, at least ninety-two percent or at least ninety-six percent of the conjugates are mono-PEG species (n equals 1) may be desired. In an embodiment of this invention the percentage of conjugates where n is 1 is from ninety percent to ninety-six percent.

The invention will be better understood by reference to the following examples which illustrate but do not limit the invention described herein.

EXAMPLE 1

Fermentation And Purification Of Human EPO a) Inoculum Preparation and Fermentation One vial of the Working Cell Bank, originating from an EPO-producing CHO cell line (ATCC CRL8695, disclosed in EP 411 678 (Genetics Institute) can be used) is taken from the gas phase of the liquid nitrogen storage tank. The cells are transferred into glass spinner flasks and cultivated in a hydrogen carbonate-buffered medium in a humidified $CO_2$ incubator. Typical serum free media used for the inoculum preparation and fermentation are disclosed in European Patent Application 513 738, to Koch published Jun. 12, 1992, or WO 96/35718, to Burg published Nov. 14, 1996, for example contain as medium DMEM/F12 (e.g. JRH Biosciences/Hazleton Biologics, Denver, US, order No. 57-736) and additionally sodium hydrogencarbonate, L+glutamine, D+glucose, recombinant insulin, sodium selenite, diaminobutane, hydrocortisone, iron(II) sulfate, asparagine, aspartic acid, serine and a stabilizer for mammalian cells such as e.g. polyvinyl alcohol, methyl cellulose, polydextran, polyethylene glycol, Pluronic F68, plasma expander polygelin (HEMACCEL®) or polyvinyl pyrrolidone (WO 96/35718).

The cultures are microscopically checked for the absence of contaminating microorganisms, and the cell densities are determined. These tests are performed at each splitting step.

After the initial growth period, the cell culture is diluted with fresh medium to the starting cell density and undergoes another growth cycle. This procedure is repeated until a culture volume of approximately 2 l per glass spinner flask has been obtained. After approx. 12 doublings 1 to 5 liter of this culture is available which then is used as inoculum for the 10 l inoculum fermenter.

After 3–5 days, the culture in the 10 l fermenter can be used as inoculum for the 100 l inoculum fermenter.

After additional 3–5 days of cultivation, the culture in the 100 l fermenter can be used as inoculum for the 1000 l production fermenter.

b) Harvesting and Cell Separation

A batch refeed process is used, i.e. when the desired cell density is reached, approx. 80% of the culture is harvested. The remaining culture is replenished with fresh culture medium and cultivated until the next harvest. One production run consists of a maximum of 10 subsequent harvests: 9 partial harvests and 1 overall harvest at the end of fermentation. Harvesting takes place every 3–4 days.

The determined harvest volume is transferred into a cooled vessel. The cells are removed by centrifugation or filtration and discarded. The EPO containing supernatant of the centrifugation step is in-line filtered and collected in a second cooled vessel. Each harvest is processed separately during purification.

A typical process for the purification of EPO-protein is disclosed in WO 96/35718, to Burg published Nov. 14, 1996. The purification process is explained in the following.

a) Blue Sepharose Chromatography

Blue Sepharose (Pharmacia) consists of Sepharose beads to the surface of which the Cibacron blue dye is covalently bound. Since EPO binds more strongly to Blue Sepharose than most non-proteinaceous contaminants, some proteinaceous impurities and PVA, EPO can be enriched in this step. The elution of the Blue Sepharose column is performed by increasing the salt concentration as well as the pH.

The column is filled with 80–100 l of Blue Sepharose, regenerated with NaOH and equilibrated with equilibration buffer (sodium/calcium chloride and sodium acetate). The acidified and filtered fermenter supernatant is loaded. After completion of the loading, the column is washed first with a buffer similar to the equilibration buffer containing a higher sodium chloride concentration and consecutively with a Tris-base buffer. The product is eluted with a Tris-base buffer and collected in a single fraction in accordance with the master elution profile.

b) Butyl Toyopearl Chromatography

The Butyl Toyopearl 650 C (Toso Haas) is a polystyrene based matrix to which aliphatic butyl-residues are covalently coupled. Since EPO binds more strongly to this gel than most of the impurities and PVA, it has to be eluted with a buffer containing isopropanol.

The column is packed with 30–40 l of Butyl Toyopearl 650 C, regenerated with NaOH, washed with a Tris-base buffer and equilibrated with a Tris-base buffer containing isopropanol.

The Blue Sepharose eluate is adjusted to the concentration of isopropanol in the column equilibration buffer and loaded onto the column. Then the column is washed with equilibration buffer with increased isopropanol concentration. The product is eluted with elution buffer (Tris-base buffer with high isopropanol content) and collected in a single fraction in accordance with the master elution profile.

c) Hydroxyapatite Ultrogel Chromatography

The Hydroxyapatite Ultrogel (Biosepra) consists of hydroxyapatite which is incorporated in an agarose matrix to improve the mechanical properties. EPO has a low affinity to hydroxyapatite and can therefore be eluted at lower phosphate concentrations than protein impurities.

The column is filled with 30–40 l of Hydroxyapatite Ultrogel and regenerated with a potassium phosphate/calcium chloride buffer and NaOH followed by a Tris-base buffer. Then it is equilibrated with a Tris-base buffer containing a low amount of isopropanol and sodium chloride.

The EPO containing eluate of the Butyl Toyopearl chromatography is loaded onto the column. Subsequently the column is washed with equilibration buffer and a Tris-base buffer without isopropanol and sodium chloride. The product is eluted with a Tris-base buffer containing a low concentration of potassium phosphate and collected in a single fraction in accordance with the master elution profile.

d) Reversed Phase HPLC on Vydac C4

The RP-HPLC material Vydac C4 (Vydac)consists of silica gel particles, the surfaces of which carry C4-alkyl chains. The separation of EPO from the proteinaceous impurities is based on differences in the strength of hydrophobic interactions. Elution is performed with an acetonitrile gradient in diluted trifluoroacetic acid.

Preparative HPLC is performed using a stainless steel column (filled with 2.8 to 3.2 liter of Vydac C4 silicagel). The Hydroxyapatite Ultrogel eluate is acidified by adding trifluoro-acetic acid and loaded onto the Vydac C4 column. For washing and elution an acetonitrile gradient in diluted trifluoroacetic acid is used. Fractions are collected and immediately neutralized with phosphate buffer. The EPO fractions which are within the IPC limits are pooled.

e) DEAE Sepharose Chromatography

The DEAE Sepharose (Pharmacia) material consists of diethylaminoethyl (DEAE)-groups which are covalently bound to the surface of Sepharose beads. The binding of EPO to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and EPO is eluted with a buffer with increased ionic strength.

The column is packed with DEAE Sepharose fast flow. The column volume is adjusted to assure an EPO load in the range of 3–10 mg EPO/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, EPO is eluted from the column with elution buffer (sodium chloride, sodium/potassium phosphate) and collected in a single fraction in accordance with the master elution profile.

The eluate of the DEAE Sepharose column is adjusted to the specified conductivity. The resulting drug substance is sterile filtered into Teflon bottles and stored at −70° C.

EXAMPLE 2

Pegylation of EPO with mPEG-SBA

EPO purified in accordance with the serum free procedure of Example 1 (EPOsf) was homogeneous as determined by analytical methods and showed the typical isoform pattern consisting of 8 isoforms. It had a specific biological activity of 190,000 IU/mg as determined by the normocythaemic mouse assay. The pegylation reagent used was a methoxy-PEG-SBA, which is a compound of Formula II in which R is methyl; x is 3; and m is from 650 to 750 (avg. about 680, corresponding to an average molecular weight of about 30 kDa).

Pegylation Reaction

To one hundred milligrams of EPOsf (9.71 ml of a 10.3 mg/ml EPOsf stock, 5.48 µmol) 10 ml of 0.1 M potassium phosphate buffer, pH, 7.5 containing 506 mg of 30 kDa methoxy-PEG-SBA (16.5 µmol) (obtained from Shearwater Polymers, Inc., Huntsville, Ala.) was added and mixed for 2 h at room temperature (20–23° C.). The final protein concentration was 5 mg/ml and the protein:PEG reagent ratio was 1:3. After two hours, the reaction was stopped by adjusting the pH to 4.5 with glacial acetic acid and stored at −20° C., until ready for purification.

Purification

1. Conjugate Mixture: Approximately 28 ml of SP-SEPHAROSE FF (sulfo-propyl cation exchange resin) was packed into an AMICON glass column (2.2×7.5 cm) and equilibrated with 20 mM acetate buffer pH, 4.5 at a flowrate of 150 ml/h. Six milliliters of the reaction mixture containing 30 mg protein was diluted 5-fold with the equilibration buffer and applied onto the column. Unadsorbed materials were washed away with the buffer and the adsorbed PEG conjugate mixture was eluted from the column with 0.175 M NaCl in the equilibration buffer. Unmodified EPOsf still remaining on the column was eluted with 750 mM NaCl. Column was reequilibrated in the starting buffer. Samples were analyzed by SDS-PAGE and their degree of pegylation were determined. It was found that the 0.175M NaCl eluate contained, mono- as well as di- and trace amounts of the tri-pegylated species, whereas the 750 mM NaCl eluate contained unmodified EPOsf.

2. Di-PEG and Mono-PEG-EPOsf: The purified conjugate mixture eluted from the column in the previous step was diluted 4-fold with the buffer and reapplied onto the column and washed as described. Di-PEG-EPOsf and mono-PEG-EPOsf were separately eluted from the column with 0.1M NaCl and 0.175 M NaCl, respectively. Elution was also performed with 750 mM NaCl to elute any remaining unmodified EPOsf.

Alternatively, the reaction mixture was diluted 5-fold with the acetate buffer and applied onto the SP-Sepharose column (~0.5 mg protein/ml gel). Column was washed and adsorbed mono-PEG-EPOsf, di-PEG-EPOsf and unmodified EPOsf were eluted as described in the previous section.

Results

PEG-EPOsf was synthesized by chemically conjugating a linear PEG molecule with a number average molecular weight of 30 kDa. PEG-EPOsf was derived from the reaction between the primary amino groups of EPOsf and the succinimidyl ester derivative of a 30 kDa PEG-butyric acid, resulting in an amide bond.

Results are summarized in Table1. Purified conjugate mixture comprised of mono- and di-PEG-EPOsf and was free of unmodified EPOsf as determined by SDS-PAGE analysis. Conjugate mixture accounted for 23.4 mg or 78% of the starting material. Cation exchange chromatographic separation of mono- and di-PEG-EPOsf indicated that mono- to di-PEG ratio in the conjugate mixture was almost 1:1. After completion of the reaction, ratio of the individual components of Mono: Di: Unmodified were 40:38:20 (%). Overall yield was almost quantitative.

TABLE 1

Summary of results of EPOsf pegylation

| Sample | Protein (mg) | Yield (%) |
| --- | --- | --- |
| Rxn. Mix. | 30 | 100 |
| Mono- | 12.0 | 40 |
| Di- | 11.4 | 38 |
| Unmod. | 6.0 | 20 |
| Conju. Mix. | 23.4 | 78 |

EXAMPLE 3

Pegylation of EPO with mPEG-SPA

A different aliquot of the EPOsf used in Example 2 was reacted with 30 kDa methoxy-PEG-SPA (Shearwater Polymers, Inc., Huntsville, Ala.). Reaction was performed at a protein:reagent ratio of 1:2 and purification techniques were in accordance with Example 2. Primarily the mono-pegylated species was produced.

EXAMPLE 4

In-vivo Activity of Pegylated EPO Determined by the Normocythaemic Mouse Assay

The normocythaemic mouse bioassay is known in the art (Pharm. Europa Spec. Issue Erythropoietin BRP Bio 1997 (2)) and a method in the monography of erythropoietin of Ph. Eur. BRP. The samples were diluted with BSA-PBS. Normal healthy mice, 7–15 weeks old, were administered s.c. 0.2 ml of the EPO-fraction containing un-pegylated EPO or tri-, di- or mono-pegylated EPO from Example 2 or 3. Over a period of 6 days, blood was drawn by puncture of the tail vein and diluted such that 1 µl of blood was present in 1 ml of an 0.15 µmol acridine orange staining solution. The staining time was 3 to 10 minutes. The reticulocyte counts were carried out microfluorometrically in a flow cytometer by analysis of the red fluorescence histogram. The reticulocyte counts were given in terms of absolute figures (per 30,000 blood cells analyzed). For the data presented, each group consisted of 5 mice per day, and the mice were bled only once.

In separate experiments, a single dose of unmodified EPO (25 ng of EPO), the PEG(SBA)-EPO mixture from Example 2 (10 ng of conjugate), mono- and di- pegylated EPOs from Example 2 (10 ng of conjugate), the PEG(SPA)-EPO from Example 3 (10 ng of conjugate), and buffer solution were administered to mice. The results are shown in Table 2. The results show the superior activity and the prolonged half life of the pegylated EPO species indicated by the significantly increased amounts of reticulocytes and the shift of the reticulocytes count maximum using the same dose per mouse (10 ng), compared to a dose of 25 ng for unmodified EPO.

TABLE 2

| | EPO (Unmodified) | 30 kDa SPA PEG | Mono 30 K SBA | Di 30 K SBA | PEG-EPO SBA Conjugate Mixture | Control Buffer |
|---|---|---|---|---|---|---|
| 72 h | 1000 | 1393 | 1411 | 994 | 1328 | 857 |
| 96 h | 500 | 1406 | 1501 | 926 | 1338 | 697 |
| 120 h | ~200 | 1100 | 1182 | 791 | 944 | 701 |
| 144 h | ~0 | 535 | 607 | 665 | 660 | 708 |

EXAMPLE 5

Preparation of Predominantly mono-PEG-EPO

Pegylation Reaction

Starting with 100 mg (5.48 μmol) of EPOsf in 100 mM potassium phosphate buffer pH 7.5 prepared in accordance with Example 1, there was added 329 mg (10.96 μmol) of 30 kDa PEG-SBA reagent dissolved in 3 ml 1 mM HCl. Enough 100 mM potassium phosphate buffer pH 7.5 was added to make the reaction mixture volume to 20 ml. The final protein concentration was 5 mg/ml and the protein: PEG reagent ratio was 1:2. The reaction mixture was mixed for 2 h at ambient temperature (20–22° C.). After 2 h, the reaction was stopped by adjusting the pH to 4.5 with glacial acetic acid and stored frozen at –20° C. until ready for purification.

Purification

The reaction mixture from the previous step was diluted 1:5 with 10 mM sodium acetate, pH 4.5 and applied to 300 ml SP-Sepharose FF (sulfopropyl cation exchange resin) packed into a 4.2×19 cm column. The column was previously equilibrated with the same buffer. Column effluents were monitored at 280 nm with a Gilson UV monitor and recorded with a Kipp and Zonen recorder. The column was washed with 300 ml or 1 bed volume of equilibration buffer to remove excess reagents, reaction byproducts and oligomeric PEG-EPO. It was followed by washing with 2 bed volumes of 100 mM NaCl to remove di-PEG-EPO. Mono-PEG-EPO was then eluted with 200 mM NaCl. During elution of the mono-PEG-EPO, the first 50 ml of the protein peak was discarded and the mono-PEG-EPO was collected as a 150 ml fraction. Unmodified EPOsf remaining on the column was eluted with 750 mM NaCl. All elution buffers were made in the equilibration buffer. All eluted samples were analyzed by SDS-PAGE and by high performance Size Exclusion Chromatography (SEC). The mono-PEG-EPO pool obtained from the 150 ml fraction, which had no detectable unmodified EPOsf, was then concentrated to ~4.5–7.5 mg/ml and diafiltered into the storage buffer, 10 mM potassium phosphate, 100 mM NaCl , pH 7.5. Concentration/Diafiltration was performed with Millipore Labscale™ TFF System fitted with 50 kDa cut off Millipore Pellicon XL Biomax 50 membrane at ambient temperature. Concentrated mono-PEG-EPO was sterile filtered and stored frozen at –20° C.

Approximately 75% of EPOsf was pegylated. After purification, total yield was ~30% mono-PEG-EPO with no detectable unmodified EPOsf and around 25% di-PEG-EPO. Oligomers, and unpegylated EPOsf accounted for the remaining protein. The mono-PEG-EPO pool obtained from the 150 ml fraction contained approximately 90% mono-PEG-EPO and approximately 10% di-PEG-EPO.

EXAMPLE 6

Thermostability of EPO and Pegylated EPO in Various Formulations: Analysis by DSC (Differential Scanning Calorimetry)

It is generally accepted that the transition temperature of thermal denaturation measured by differential scanning calorimetry is a valid indicator for the thermostability of proteins. Erythropoietin or pegylated erythropoietin (prepared according to Example 3) solutions with concentrations between 0.6 and 1.2 mg/ml were analyzed in various buffers with or without stabilizers by means of a Nano-DSC (Calorimetric Sciences Corporation, Utah, USA) at a heating rate of 2 K/min. An increase in transition temperature indicates an increase in thermal stability of the protein. The measured temperature values should not be understood as absolute values but rather represent differences in the stability of the individual formulations relative to one another.

In order to define the optimal pH of the formulation, the pH-dependence of the thermal denaturation of pegylated erythropoietin in the range between 4 and 9 was studied. The protein samples were analyzed in 30 mM $Na_2HPO_4$, 30 mM sodium citrate, 30 mM borate. FIG. 1 shows a plateau of maximal transition temperature between about pH 6 to about pH 9 and a sharp decrease below pH 5.5. This indicates that the optimal pH for maximal thermal stability lies above pH 5.5. (FIG. 1).

Figure 2:
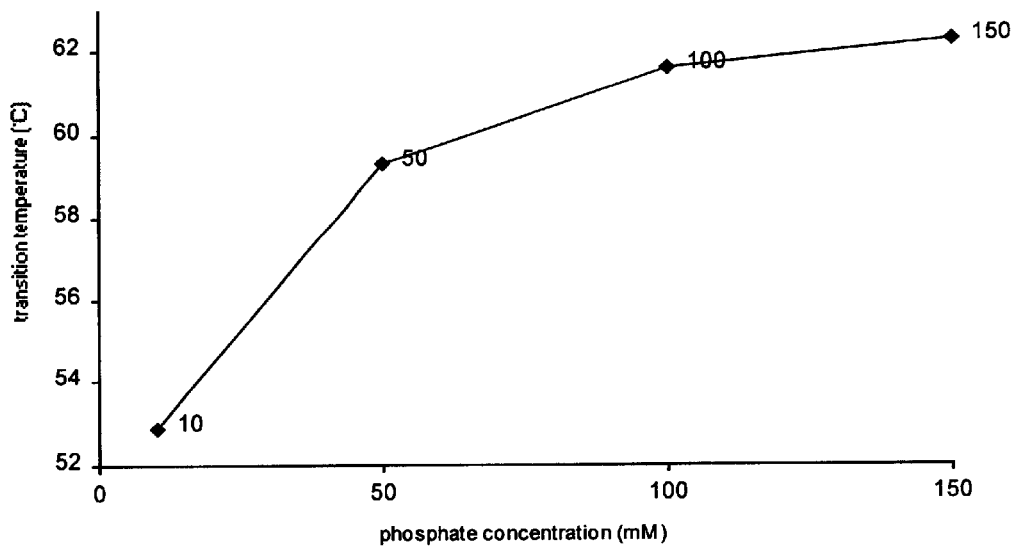
FIG. 2: Influence of ionic strength on thermal stability. The transition temperature is plotted against the phosphate concentration.

In order to investigate the effect of ionic strength, the phosphate concentration dependence of thermal denaturation was determined. FIG. 2 shows that the thermal stability increases with an increase in ionic strength of the formulation.

Figure 3:
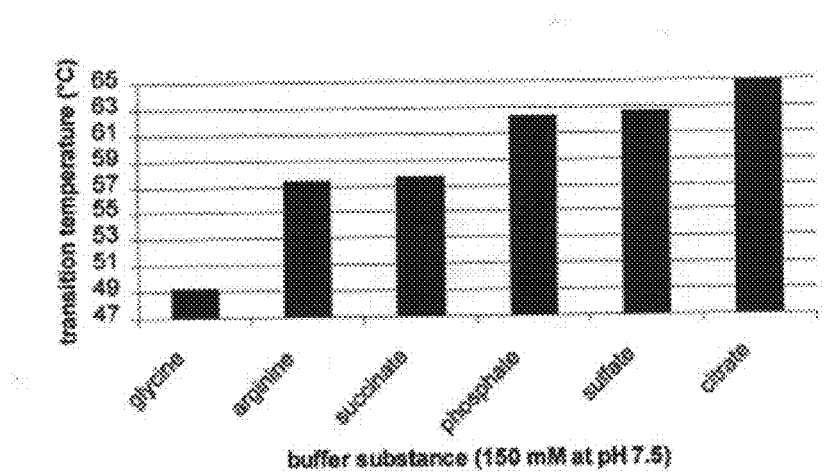
FIG. 3: Dependence of thermal stability on buffer substance.

The influence of the buffer substance was also investigated by DSC. From FIG. 3 one can see that the most suitable buffers or additives for a high thermal stability are sulfate, citrate or phosphate. Glycine, which is used as a buffer in currently available formulations (see above) is not very suitable.

Figure 4:
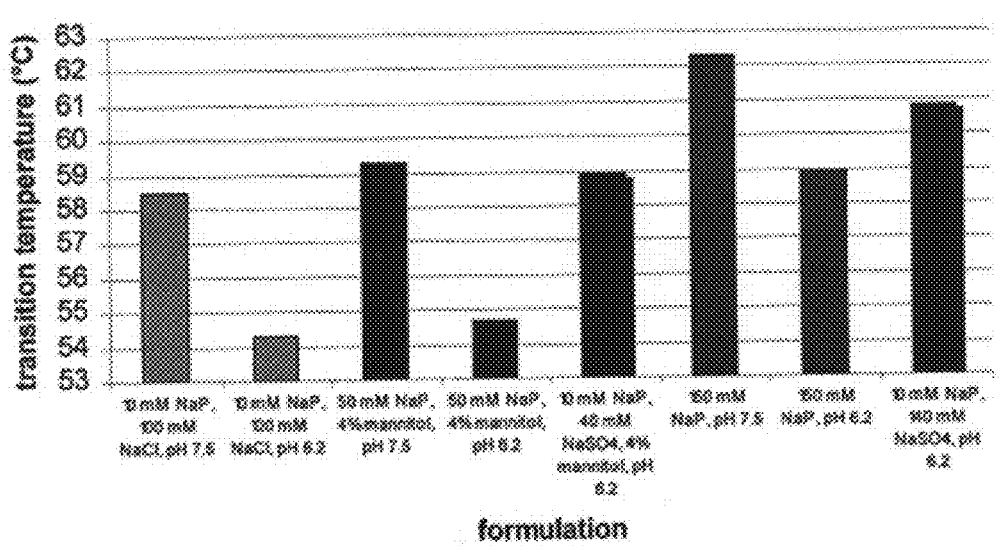
FIG. 4 shows that sulfate is also a suitable buffer/additive at low pH (e.g. pH 6.2), whereas phosphate is less suitable at pH 6.2 compared to pH 7.5. This shows that sulfate keeps the thermal stability high, even at low pH.

FIG. 4 shows that sulfate is also a suitable buffer/additive at low pH (e.g. pH 6.2), whereas phosphate is less suitable at pH 6.2 compared to pH 7.5. This shows that sulfate keeps the thermal stability high, even at low pH. This finding allows a formulation at a pH between 6.0 and 6.5, without severe losses in thermal stability of erythropoietin.

EXAMPLE 7

Aggregation of EPO and peg-EPO Under Thermal Stress: Analysis by SDS-PAGE (Sodium Dodecyl Sulphate Polyacrylamide Gel Electrophoresis)

Figure 5:
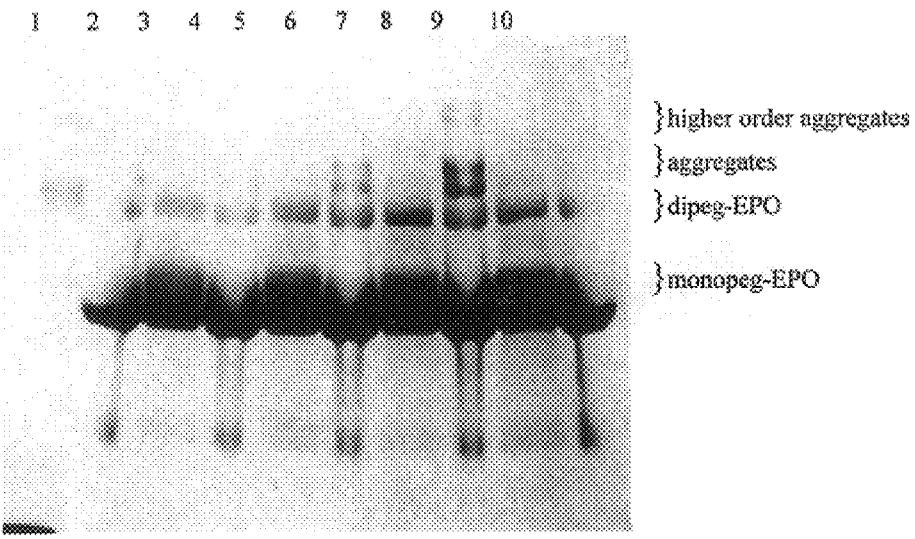
FIG. 5: Dependency of peg-EPO aggregation on pH. Peg-EPO samples after heat stress (as described above) were analyzed by SDS-PAGE. Proteins were stained with silver. Lane 1: molecular weight standard. Lane 2: pH 5. Lane 3: pH 5, reduced. Lane 4: pH 6. Lane 5: pH 6, reduced. Lane 6: pH 6.5. Lane 7: pH 6.5, reduced. Lane 8: pH 7. Lane 9: pH 7, reduced. Lane 10: peg-EPO, unstressed.

In order to investigate the effect of heat stress on the erythropoietin protein, samples in different formulations were exposed to heat stress (20 min 80° C.) and analyzed by sodium dodecyl sulphate polyacrylamide gel electrophoresis (SDS-PAGE) under reducing (with DTT in sample buffer) and non-reducing (w/o DTT in sample buffer) conditions. This method allows the detection of covalent aggregate formation. As outlined above, aggregate formation is one of the major degradation pathways of proteins and therefore should be prevented in pharmaceutical formulations of proteins. Aggregates that are detectable in the absence of reducing agent (e.g. DTT) and not detectable in the presence of reducing agent are highly likely to be formed by incorrect disulfide bridging, an oxidation reaction, under heat stress. FIG. 5 shows the pH dependency of aggregation under heat stress. This experiment clearly shows that the formation of aggregates is suppressed at a pH below 6.5. The higher the pH, the higher the amount of aggregation. Most of the aggregates that are formed can be reduced by treatment of the samples with a reducing agent during SDS-PAGE, suggesting that a great portion of the aggregates that are formed under heat stress are disulfide-bridged dimers, oligomers and higher order aggregates. Taken together, his indicates that the formation of aggregates can be prevented to a great extent by keeping the pH of the formulation at or below pH 6.5.

FIG. 5: Dependency of peg-EPO aggregation on pH. Peg-EPO samples prepared accord to Example 3 were subjected to heat stress (as described above) and then analyzed by SDS-PAGE. Proteins were stained with silver. Lane 1: molecular weight standard. Lane 2: pH 5. Lane 3: pH 5, reduced. Lane 4: pH 6. Lane 5: pH 6, reduced. Lane 6: pH 6.5. Lane 7: pH 6.5, reduced. Lane 8: pH 7. Lane 9: pH 7, reduced. Lane 10: peg-EPO, unstressed.

Figure 6:
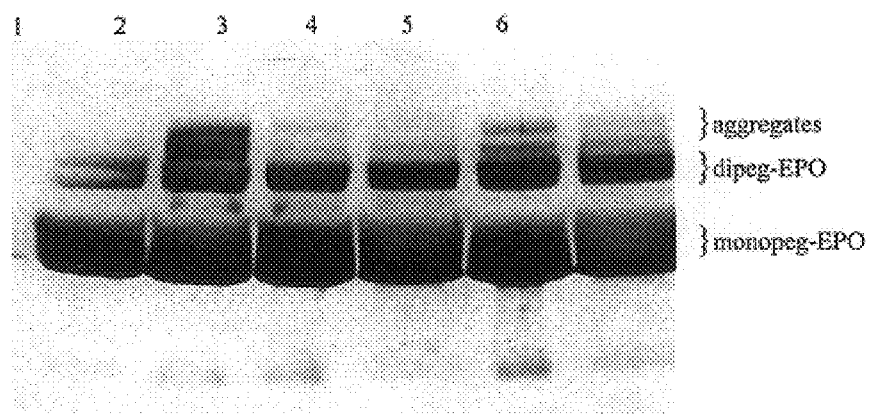
FIG. 6 shows that the use of 1 mg/ml acetylcysteine as an antioxidant prevents the formation of aggregates under heat stress.

The formation of aggregates can also be prevented by the use of antioxidants. FIG. 6 shows that the use of 1 mg/ml acetylcysteine as an antioxidant prevents the formation of aggregates under heat stress. Therefore, it is useful to use an antioxidant, like e.g. acetylcysteine at a low pH, e.g. pH 6.2, to prevent aggregate formation under heat stress.

FIG. 6: Peg-EPO aggregation can be prevented by pH 6.2 and/or acetylcysteine. Peg-EPO samples prepared according to Example 3 were subjected to heat stress (as described above) and then analyzed by SDS-PAGE. Proteins were stained with silver. Lane 1: peg-EPO, unstressed. Lane 2: pH 7.5, stressed. Lane 3: pH 6.2, stressed. Lane 4: pH 6.2, stressed, reduced. Lane 5: pH 7.5, 1 mg/ml acetylcysteine, stressed. Lane 6: pH 7.5, 1 mg/ml acetylcysteine, stressed, reduced.

EXAMPLE 8

Stability of peg-EPO in Various Formulations at 4, 25, 30 and 40° C.

Pegylated EPO prepared according to Example 3 in various formulations is incubated at several temperatures. At indicated time points, samples are taken and the stability is assessed by reversed phase high performance chromatography (rpHPLC), high performance size exclusion chromatography (SEC) and sodium dodecyl sulphate polyacrylamide gel electrophoresis (SDS-PAGE). Table 3 compares the stability of peg-EPO in various formulations at several temperatures. These data clearly show the superiority of the herein enclosed formulations regarding protein recovery and aggregation.

TABLE 3

Stability of peg-EPO in various formulations at several temperatures:

| Formulation* | PegEPO (µg/ml) | % recovery after one month at | | | | Aggregation at 40° C. detectable (+/−) |
|---|---|---|---|---|---|---|
| | | 4° C. | 25° C. | 30° C. | 40° C. | |
| A | 10 | 95 | 92 | n.d. | 66 | − |
| B | 10 | 93 | 90 | n.d. | 64 | − |
| C | 10 | 115 | 115 | 111 | 105 | − |
| D | 10 | 100 | 99 | 102 | 93 | − |
| E | 50 | n.d. | 106 | 99 | 84 | + |
| F | 50 | 98 | 100 | 98 | 89 | − |
| G | 50 | 101 | 101 | 101 | 100 | − |
| H | 50 | 105 | 103 | 101 | 102 | − |
| I | 50 | 103 | 101 | 104 | 104 | − |
| A | 100 | 100 | 99 | n.d. | 79 | + |
| B | 100 | 103 | 100 | n.d. | 77 | + |
| C | 100 | 103 | 102 | 103 | 88 | − |
| D | 100 | 105 | 106 | 106 | 98 | − |
| E | 400 | 98 | 96 | 89 | 88 | + |
| F | 400 | 99 | 97 | 96 | 93 | − |
| G | 400 | 98 | 96 | 100 | 106 | − |
| H | 400 | 107 | 108 | 102 | 97 | − |
| I | 400 | 104 | 105 | 98 | 103 | − |

*the formulations are:

formulation A: 10 mM sodium phosphate, 100 mM sodium chloride, pH 7.5.

formulation B: 200 mM glycine, pH 7.1.

formulation C: 10 mM sodium phosphate, 140 mM sodium sulfate, pH 6.2.

formulation D: 10 mM sodium phosphate, 40 mM sodium sulfate, 4% (w/v) mannitol, pH 6.2.

formulation E: 10 mM sodium phosphate, 100 mM NaCl, pH 7.0.

formulation F: 10 mM sodium phosphate, 120 mM sodium sulfate, pH 6.2 formulation G: 10 mM sodium phosphate, 40 mM sodium sulfate, 3% (w/v) mannitol, pH 6.2.

formulation H: 10 mM sodium phosphate, 40 mM sodium sulfate, 3% (w/v) mannitol, 7.5 µM CaCl$_2$, pH 6.2.

formulation I: 50 mM arginine, 100 mM sodium sulfate, 1 mM CaCl$_2$, pH 6.2.

What is claimed is:

1. A conjugate comprising an erythropoietin glycoprotein having a free amino group and having the in vivo biological activity of causing bone marrow cells to increase production of reticulocytes and red blood cells and selected from the group consisting of human erythropoietin and analogs thereof which analogs have sequence of human erythropoietin modified by the addition of from 1 to 6 glycosylation sites or a rearrangement of at least one glycosylation site; said glycoprotein being covalently linked to a poly(ethylene glycol) group of the formula $—CO—(CH_2)_x—(OCH_2CH_2)_m—OR$ by the $—CO$ of said poly(ethylene glycol) group forming an amide bond with said free amino group; wherein R is lower alkyl; x is 2 or 3; m is from about 450 to about 900; and m is chosen so that the molecular weight of the conjugates minus the erythropoietin glycoprotein is from 20 kilodaltons to 100 kilodaltons.

2. The conjugate of claim 1 of the formula:

$$P—NHCO—(CH_2)_x—(OCH_2CH_2)_m—OR \quad (I)$$

wherein m, x and R are as above
and P is the residue of the glycoprotein without the free amino group which forms the amide linkage.

3. The conjugate of claim 2 wherein the glycoprotein is human erythropoietin.

4. The conjugate of claim 3, wherein the human erythropoietin glycoprotein is expressed by endogenous gene activation.

5. The conjugate of claim 3, wherein the glycoprotein has the sequence SEQ ID NO:1.

6. The conjugate of claim 5, wherein R is methyl.

7. The conjugate of claim 5 wherein x is 3.

8. The conjugate of claim 7 wherein said molecular weight is from about 20 kDa to about 4kDa.

9. The conjugate of claim 8 wherein said molecular weight is about 30 kDa.

10. The conjugate of claim 2, wherein the glycoprotein has the sequence of human erythropoietin modified by the addition of from 1 to 6 glycosylation sites.

11. The conjugate of claim 10, wherein the glycoprotein has the sequence of human erythropoietin modified by a modification selected from the group consisting of:

$Asn^{30}Thr^{32}$;
$Asn^{51}Thr^{53}$;
$Asn^{57}Thr^{59}$;
$Asn^{69}$;
$Asn^{69}Thr^{71}$;
$Ser^{68}Asn^{69}Thr^{71}$;
$Val^{87}Asn^{88}Thr^{90}$;
$Ser^{87}Asn^{88}Thr^{90}$;
$Ser^{87}Asn^{88}Gly^{89}Thr^{90}$;
$Ser^{87}Asn^{88}Thr^{90}Thr^{92}$;
$Ser^{87}Asn^{88}Thr^{90}Ala^{162}$;
$Asn^{69}Thr^{71}Ser^{87}Asn^{88}Thr^{90}$;
$Asn^{30}Thr^{32}Val^{87}Asn^{88}Thr^{90}$;
$Asn^{89}Ile^{90}Thr^{91}$;
$Ser^{87}Asn^{89}Ile^{90}Thr^{91}$;
$Asn^{136}Thr^{138}$;
$Asn^{138}Thr^{140}$;
$Thr^{125}$; and
$Pro^{124}Thr^{125}$.

12. The conjugate of claim 2, wherein the glycoprotein has the sequence of human erythropoietin modified by the rearrangement of at least one glycosylation site.

13. The conjugate of claim 12, wherein the rearrangement comprises deletion of any of the N-linked glycosylation sites in human erythropoietin and addition of an N-linked glycosylation site at position 88 of the sequence of human erythropoietin.

14. The conjugate of claim 13, wherein the glycoprotein has the sequence of human erythropoietin modified by a modification selected from the group consisting of:
$Gln^{24}Ser^{87}Asn^{88}Thr^{90}$;
$Gln^{38}Ser^{87}Asn^{88}Thr^{90}$; and
$Gln^{83}Ser^{87}Asn^{88}Thr^{90}$.

15. The conjugate of claim 14, wherein R is methyl.

* * * * *

UNITED STATES PATENT AND TRADEMARK OFFICE
CERTIFICATE OF CORRECTION

| | | |
|---|---|---|
| PATENT NO. | : 6,583,272 B1 | Page 1 of 1 |
| APPLICATION NO. | : 09/604938 | |
| DATED | : June 24, 2003 | |
| INVENTOR(S) | : Pascal Sebastian Bailon | |

It is certified that error appears in the above-identified patent and that said Letters Patent is hereby corrected as shown below:

IN THE CLAIMS:

Column 19, line 48: "4kDa" should read -- 40kDa -- .

Signed and Sealed this

Twenty-second Day of May, 2007

JON W. DUDAS
*Director of the United States Patent and Trademark Office*